(12) United States Patent
Gupta et al.

(10) Patent No.: US 11,517,459 B2
(45) Date of Patent: Dec. 6, 2022

(54) DELIVERY SYSTEM FOR ENDOVASCULAR DEVICES

(71) Applicant: Monarch Biosciences, Inc., Los Angeles, CA (US)

(72) Inventors: Vikas Gupta, Los Angeles, CA (US); Colin Kealey, Los Angeles, CA (US)

(73) Assignee: MONARCH BIOSCIENCES, INC., Los Angeles, CA (US)

( * ) Notice: Subject to any disclaimer, the term of this patent is extended or adjusted under 35 U.S.C. 154(b) by 9 days.

(21) Appl. No.: 16/951,367

(22) Filed: Nov. 18, 2020

(65) Prior Publication Data

US 2022/0151809 A1    May 19, 2022

(51) Int. Cl.
*A61F 2/97* (2013.01)
*A61F 2/966* (2013.01)

(52) U.S. Cl.
CPC .............. *A61F 2/97* (2013.01); *A61F 2/966* (2013.01)

(58) Field of Classification Search
CPC .. A61F 2/95; A61F 2/962; A61F 2/966; A61F 2/97; A61F 2002/9623; A61F 2002/9665
See application file for complete search history.

(56) References Cited

U.S. PATENT DOCUMENTS

| | | | |
|---|---|---|---|
| 2002/0099435 A1* | 7/2002 | Stinson ...................... | A61F 2/97 623/1.12 |
| 2012/0059448 A1* | 3/2012 | Parker ....................... | A61F 2/95 141/2 |
| 2012/0065660 A1* | 3/2012 | Ferrera ..................... | A61F 2/01 606/198 |
| 2012/0143303 A1* | 6/2012 | Dorn ........................ | A61F 2/966 623/1.12 |
| 2018/0242978 A1* | 8/2018 | Chou ............... | A61B 17/12109 |

FOREIGN PATENT DOCUMENTS

WO    WO 2018/005473    1/2018

* cited by examiner

*Primary Examiner* — Diane D Yabut
(74) *Attorney, Agent, or Firm* — Haynes and Boone, LLP

(57) ABSTRACT

Systems, methods, and apparatus for delivery systems for endovascular devices are disclosed herein. In one or more embodiments, a delivery system comprises a stent comprising a mesh. Further, the delivery system comprises a shaft comprising an inner lumen. Also, the delivery system comprises a sheath encasing the stent. In one or more embodiments, the stent and a first portion of the sheath is connected to an end of a wire, and a second portion of the sheath is folded back and connected to an end of the shaft. Further, the delivery system comprises the wire traversing within the inner lumen of the shaft such that when the shaft is pulled back relative to the wire, the sheath splits open thereby unsheathing and deploying the stent.

18 Claims, 18 Drawing Sheets

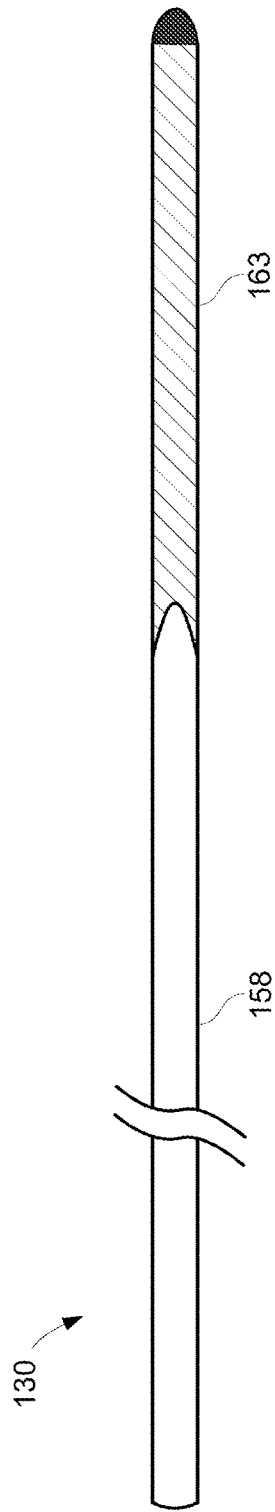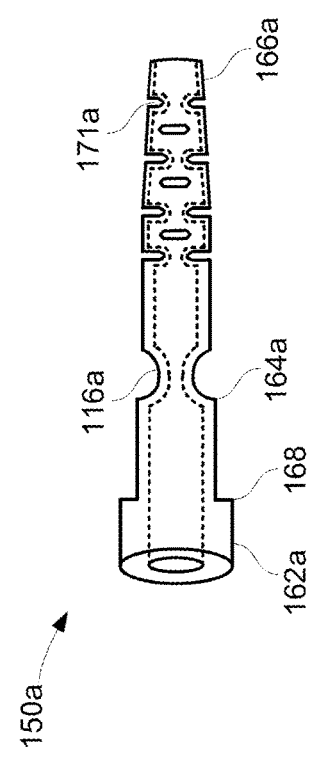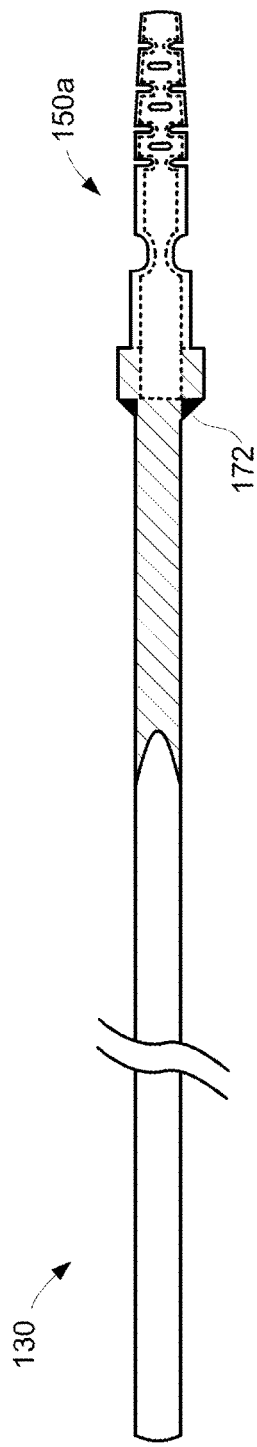

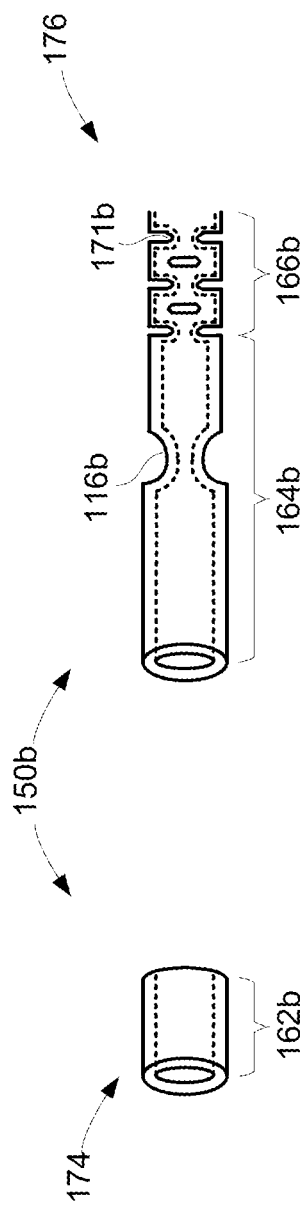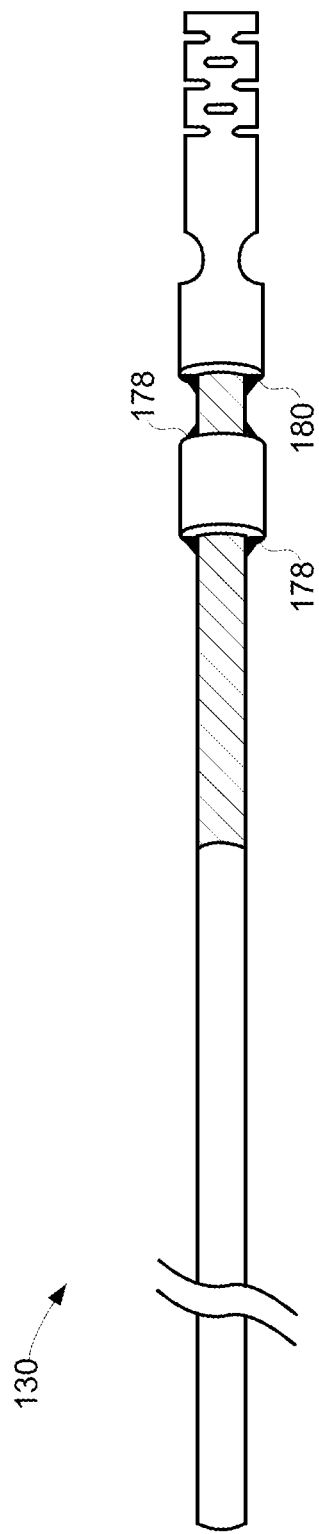

DELIVERY SYSTEM FOR ENDOVASCULAR DEVICES

TECHNICAL FIELD

The present disclosure generally relates to medical devices and, more particularly, to delivery systems for endovascular devices.

BACKGROUND

Endovascular devices must be compressed and inserted into small diameter catheters to be delivered via minimally-invasive means throughout the body. This can be difficult because endovascular devices may exert a radial force on the wall of the catheter, and must be pushed through very tortuous anatomy. This can cause significant friction, limiting the ability of operators to efficiently deliver devices to the desired anatomical target. Common strategies to improve endovascular device delivery have focused on decreasing friction between the catheter wall and the device. This is commonly accomplished with low friction, hydrophilic, and lubricious inner linings of catheters (polytetrafluoroethylene (PTFE) is commonly used for this purpose), as well as surface modifications of the device being delivered.

This problem is particularly acute for covered stents (e.g., thin-film covered stents) where there is a large amount of material that must be compressed into the catheter. The high amount of surface area of the stent covering increases the friction between the stent and catheter wall so that delivering covered stents can be more challenging than their non-covered counterparts.

Therefore, there is a need for an improved delivery system for endovascular devices.

SUMMARY

The present disclosure relates to methods, systems, and apparatuses for a delivery system for endovascular devices. In one or more embodiments, a method for operating a delivery system comprises pulling back on a shaft relative to a wire, which traverses within an inner lumen of the shaft, such that a sheath, which encases a stent and is connected to the shaft and the wire, splits open to unsheathe and deploy the stent.

In one or more embodiments, a distance of pulling back of the shaft in relation to a distance of unsheathing of the stent is approximately a two to one ratio, such that every two units of distance of pulling back of the shaft causes approximately one unit of distance of unsheathing of the stent.

In at least one embodiment, the method further comprises releasing the stent from the wire, when the stent is fully unsheathed, to deploy the stent.

In one or more embodiments, a delivery system comprises a stent comprising a mesh. The system further comprises a shaft comprising an inner lumen. Also, the system comprises a sheath encasing the stent. In one or more embodiments, the stent and a first portion of the sheath is connected to an end of a wire, and a second portion of the sheath is folded back and connected to an end of the shaft. Further, the system comprises the wire traversing within the inner lumen of the shaft such that when the shaft is pulled back relative to the wire, the sheath splits open thereby unsheathing and deploying the stent.

In at least one embodiment, the second portion of the sheath, which is folded back, is split. In some embodiments, the stent is connected to the wire via a delivery tip. In at least one embodiment, the delivery tip comprises a hole and/or a groove.

In one or more embodiments, the sheath comprises polytetrafluoroethylene (PTFE). In some embodiments, the mesh comprises a metallic material. In at least one embodiment, the metallic material is one of nitinol or stainless steel.

In at least one embodiment, the shaft comprises an outer jacket, an inner liner, and a braided tubing. In one or more embodiments, the outer jacket comprises a thermoplastic elastomer (TPE) material. In some embodiments, the inner liner comprises PTFE. In at least one embodiment, the braided tubing comprises a braided mesh of wires. In one or more embodiments, the wire comprises stainless steel, nitinol, and/or tungsten.

In one or more embodiments, the shaft comprises a laser-cut stainless-steel hypotube. In at least one embodiment, the laser-cut stainless-steel hypotube comprises a plurality of laser cuts, where the density of the laser cuts varies along a length of the shaft. In some embodiments, the flexibility of the shaft is related (e.g., directly proportional) to the density of the laser cuts.

In one or more embodiments, a method for manufacture of a delivery system comprises traversing a wire within an inner lumen of a shaft. The method further comprises connecting a stent, which comprises a mesh, to the end of the wire via a delivery tip. Also, the method comprises encasing the stent within a sheath, which is tubular in shape. In addition, the method comprises attaching a first portion of the sheath to an end of the wire. Additionally, the method comprises splitting a second portion of the sheath longitudinally into two halves. Also, the method comprises folding back the two halves of the sheath. Further, the method comprises attaching an end of each of the two halves of the sheath to an end of the shaft.

BRIEF DESCRIPTION OF DRAWINGS

These and other features, aspects, and advantages of the present disclosure will become better understood with regard to the following description, appended claims, and accompanying drawings where:

FIGS. 1A, 1B, 1C, 1D, 1E, 1F, 1G, 1H, 1I, 1J, 1K, 2, and 3 are diagrams that together illustrate details and the operation of the disclosed delivery system for endovascular devices, in accordance with various embodiments of the present disclosure.

FIG. 1A is a diagram showing the disclosed delivery system for endovascular devices, where the sheath is intact and enclosed within a catheter, in accordance with at least one embodiment of the present disclosure.

FIG. 1B is a diagram showing details of an exemplary shaft of the delivery system of FIG. 1A, in accordance with at least one embodiment of the present disclosure.

FIG. 1C is a diagram showing details of an exemplary wire of the delivery system of FIG. 1A, in accordance with at least one embodiment of the present disclosure.

FIG. 1D is a diagram showing details of an exemplary one-piece delivery tip of the delivery system of FIG. 1A, in accordance with at least one embodiment of the present disclosure.

FIG. 1E is a diagram showing details of the one-piece delivery tip of FIG. 1D assembled on the wire of FIG. 1C of the delivery system of FIG. 1A, in accordance with at least one embodiment of the present disclosure.

FIGS. 1F and 1G are diagrams showing details of an exemplary two-piece delivery tip of the delivery system of FIG. 1A, in accordance with at least one embodiment of the present disclosure.

FIG. 1H is a diagram showing details of the two-piece delivery tip of FIGS. 1F and 1G assembled on the wire of FIG. 1C of the delivery system of FIG. 1A, in accordance with at least one embodiment of the present disclosure.

FIG. 1I is an image of an exemplary laser-cut shaft that may be employed for the shaft of FIG. 1A, in accordance with at least one embodiment of the present disclosure.

FIG. 1J is an image of another exemplary laser-cut shaft that may be employed for the shaft of FIG. 1A, in accordance with at least one embodiment of the present disclosure.

FIG. 1K is a schematic diagram showing details of an exemplary laser-cut shaft that may be employed for the shaft of FIG. 1A, in accordance with at least one embodiment of the present disclosure.

FIG. 2 is a diagram showing the disclosed delivery system of FIG. 1A, where the sheath is split open and the stent is partially unsheathed, in accordance with at least one embodiment of the present disclosure.

FIG. 3 is a diagram showing the disclosed delivery system of FIG. 1A, where the stent is fully deployed, in accordance with at least one embodiment of the present disclosure.

FIG. 6 is a diagram showing the stent encased within the sheath for the disclosed delivery system for endovascular devices, in accordance with at least one embodiment of the present disclosure.

FIG. 7 is a diagram showing a portion of the sheath split longitudinally into two halves for the disclosed delivery system for endovascular devices, in accordance with at least one embodiment of the present disclosure.

FIG. 8 is a diagram showing the two halves of the sheath folded back and attached to an end of the shaft for the disclosed delivery system for endovascular devices, in accordance with at least one embodiment of the present disclosure.

Figure 1A:
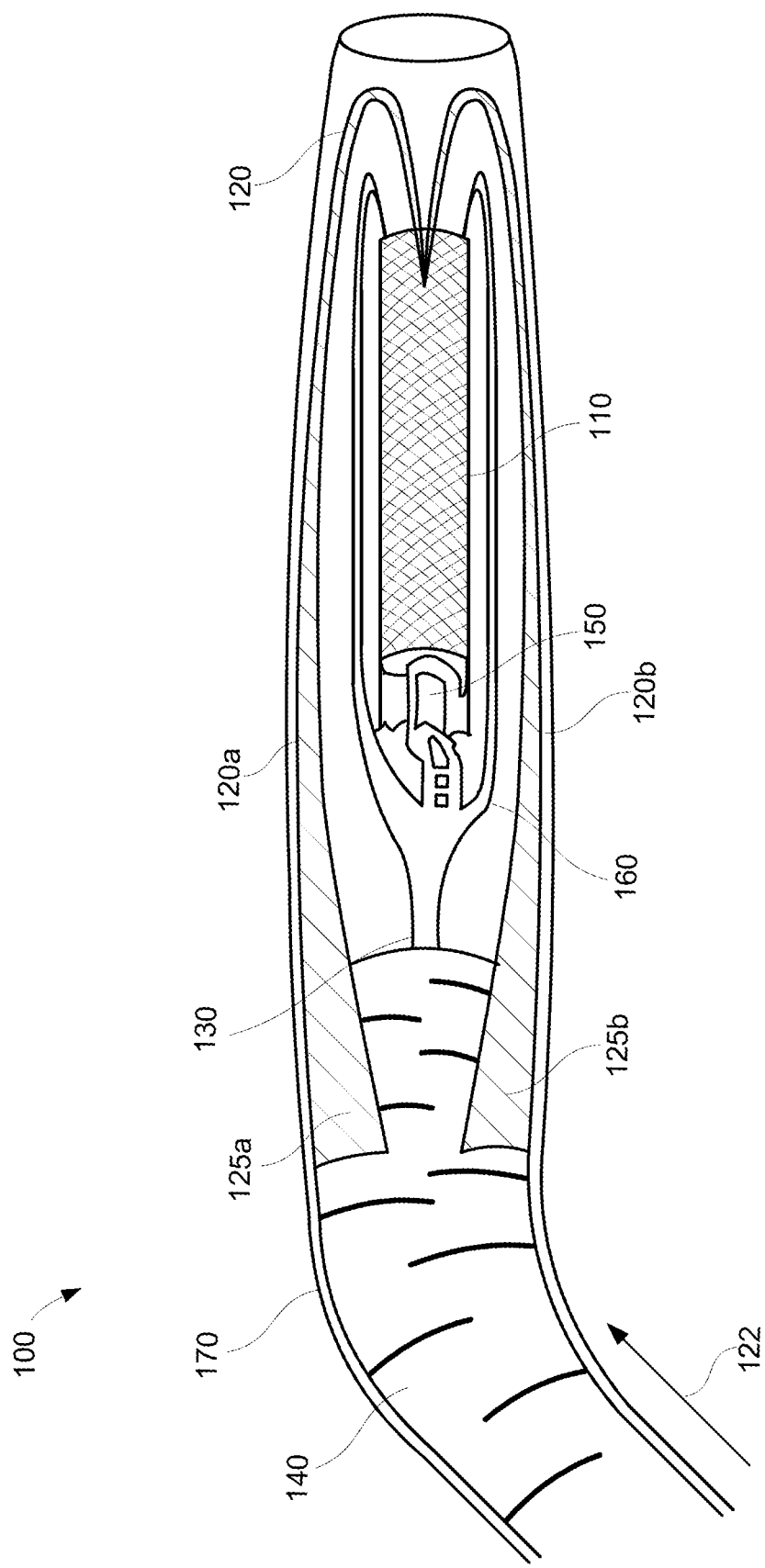

Embodiments of the present disclosure and their advantages are best understood by referring to the detailed description that follows. It should be appreciated that like reference numerals are used to identify like elements illustrated in one or more of the figures, in which the showings therein are for purposes of illustrating the embodiments and not for purposes of limiting them.

DETAILED DESCRIPTION

The methods and apparatuses disclosed herein provide operative systems for delivery systems for endovascular devices. In one or more embodiments, the system of the present disclosure comprises an improved delivery device for delivering a thin-film flow diverter (e.g., a metallic micromesh stent) to neurovascular of a patient. The disclosed delivery device is designed to fit into a 0.027 inch industry-standard microcatheter.

Currently, with conventional delivery devices, excessive friction between the conventional delivery device and the catheter wall prevents pushing the conventional delivery device from the groin to the head. Friction is a problem with all of these conventional delivery devices, but for use with a thin film-flow diverter, it is even worse because the stent is covered with a metallic micromesh that, when crimped down to fit within a catheter, forms a huge number of edges and surface area that drags against the catheter wall.

To solve the problem of excessive friction during delivery, the disclosed delivery device employs a PTFE sheath that is circumferentially intact, thereby preventing the delivery device from exerting an outward radial force on the catheter wall. The distal end of the PTFE sheath is split into two equal halves, and folded back proximally, where it is attached to a shaft (e.g., a laser-cut stainless-steel hypotube). The PTFE sheath encases the stent, and only the very distal end of the stent is exposed from the PTFE sheath. The stent itself is coupled to a wire, which runs through the center of the hypotube, via a delivery tip. To deploy the stent, the operator (e.g., a physician or clinician) tracks the stent through the distal end of the catheter so that only the very tip of the stent is exposed. The catheter and the hypotube are then coupled to each other via a rotating hemostatic valve (RHV) hub or other suitable method, and the wire traversing within the center of the hypotube is fixed in place, while the catheter/hypotube are pulled back together. Pulling back the hypotube/catheter relative to the inner wire splits open the PTFE sheath that is encasing the stent and, thus, allows the stent to deploy.

It should be noted that it should not be necessary to couple the catheter and the hypotube together as long as the stent is outside the catheter. Practically, however, the catheter helps support the stent during the PTFE sheath splitting process. Also, it should be noted that since the PTFE sheath is folded back on itself, the catheter/hypotube must move back two (2) units of distance for every one (1) unit of stent that is unsheathed.

In addition, it should be noted that a "steerable" inner wire is employed for the disclosed delivery device. Also, to reduce friction, the inner lumen of the hypotube (shaft) needs to be as smooth as possible to allow for the inner wire and shaft to move easily relative to each other.

In the following description, numerous details are set forth in order to provide a more thorough description of the system. It will be apparent, however, to one skilled in the art, that the disclosed system may be practiced without these specific details. In the other instances, well known features have not been described in detail, so as not to unnecessarily obscure the system.

For the sake of brevity, conventional techniques and components related to delivery systems, and other functional aspects of the overall system may not be described in detail herein. Furthermore, the connecting lines shown in the various figures contained herein are intended to represent example functional relationships and/or physical couplings between the various elements. It should be noted that many alternative or additional functional relationships or physical connections may be present in one or more embodiments of the present disclosure.

Embodiments of the present disclosure may be described herein in terms of functional components and various processing steps. Those skilled in the art will appreciate that embodiments of the present disclosure may be practiced in conjunction with other components, and that the systems described herein are merely example embodiments of the present disclosure.

FIGS. 1A, 1B, 1C, 1D, 1E, 1F, 1G, 1H, 1I, 1J, 1K, 2, and 3 are diagrams that together illustrate details and the operation of the disclosed delivery system 100 for endovascular devices, in accordance with various embodiments of the present disclosure. In particular, FIG. 1A is a diagram showing the disclosed delivery system 100 for endovascular devices, where the sheath 120 is intact and enclosed within a catheter 170, in accordance with at least one embodiment of the present disclosure.

Figure 6:
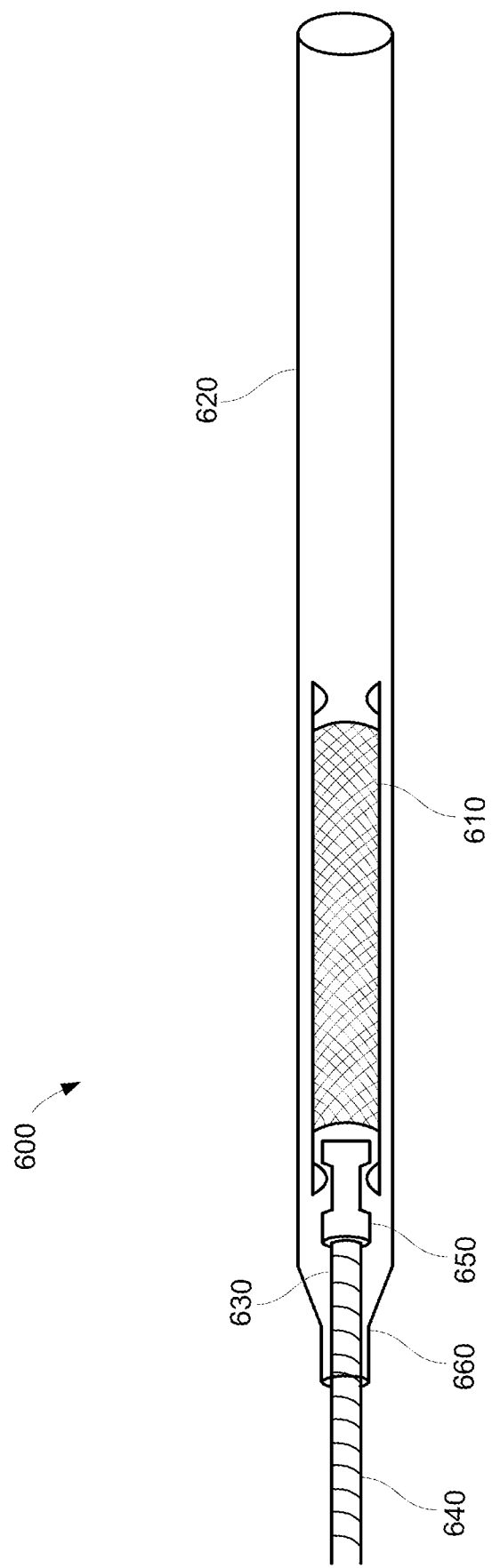
FIGS. 6, 7, and 8 are diagrams that together illustrate a portion of the method of manufacture of the delivery system for endovascular devices, in accordance with at least one embodiment of the present disclosure.
Figure 7:
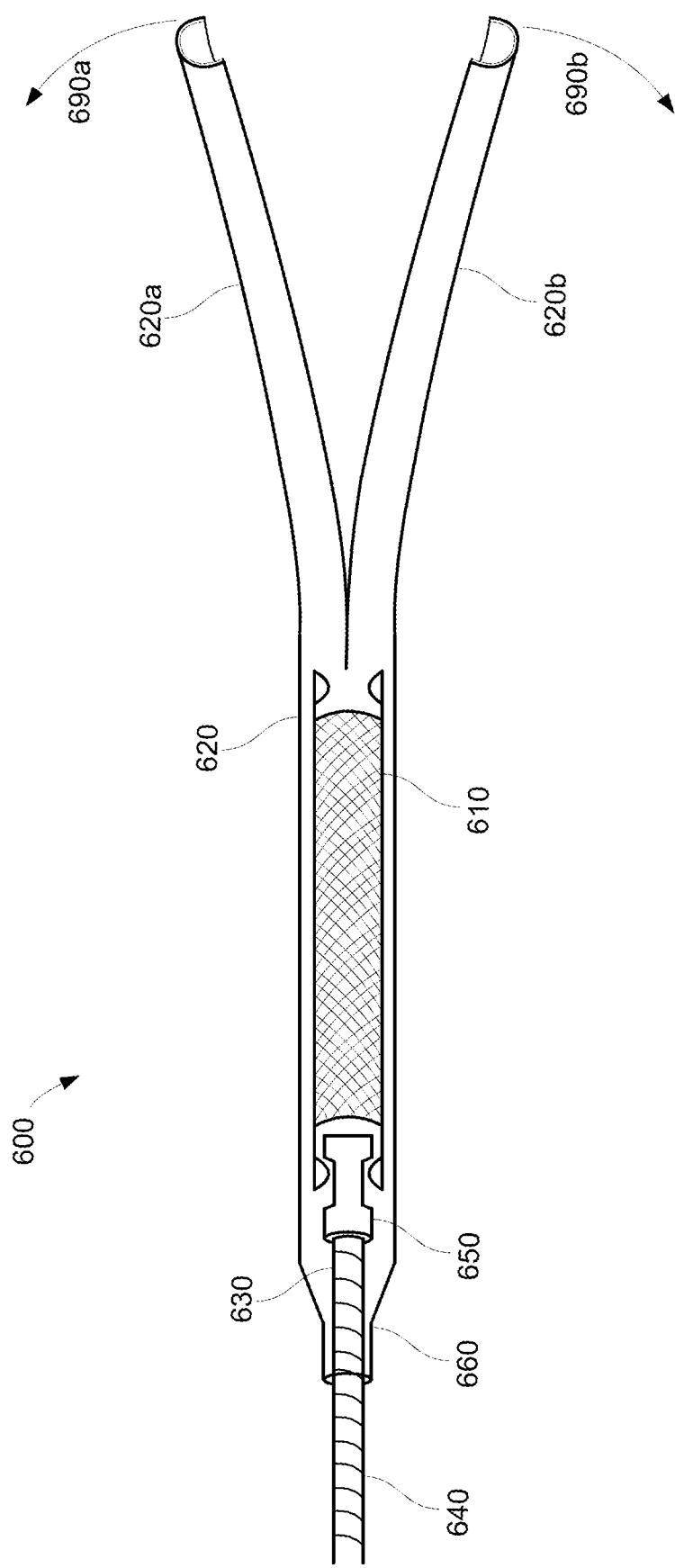
Figure 8:
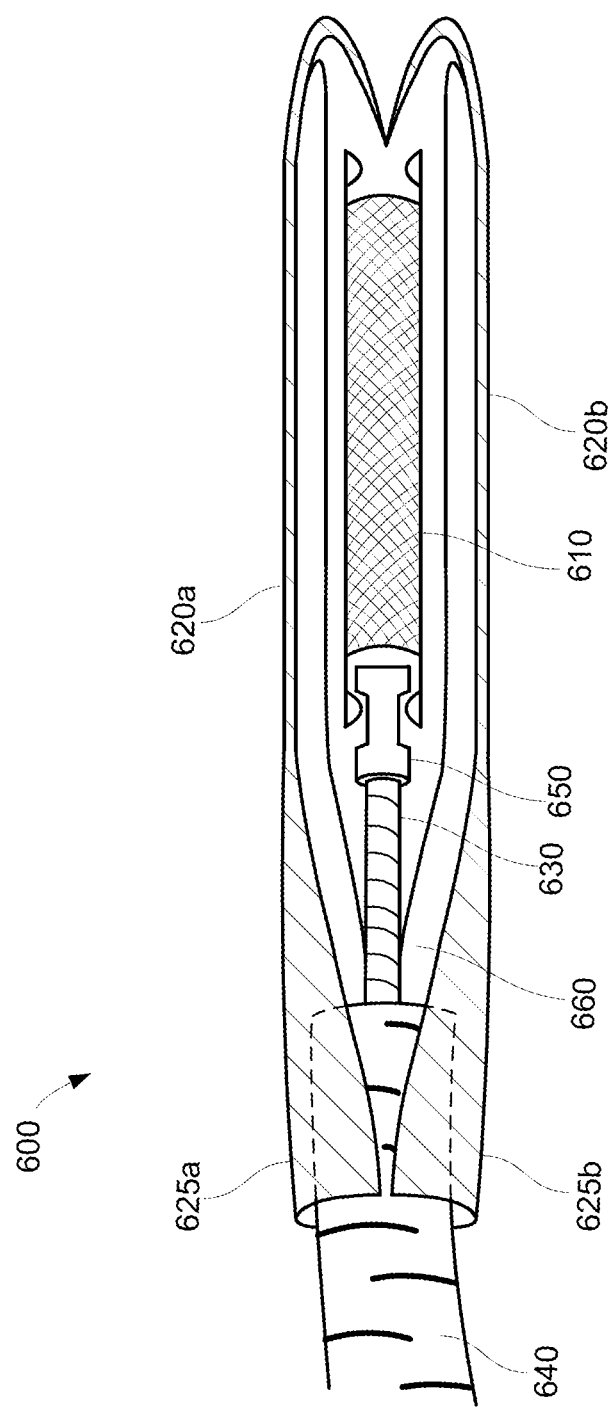

In FIG. 1A, the delivery system 100 includes a sheath (e.g., a delivery sheath) 120 that is tubular (e.g., approximately cylindrical) in shape, and forms an inner lumen therethrough. A portion (e.g., a first portion) of the sheath 120 is circumferentially intact, where an end 160 of the portion (e.g., the first portion) of the sheath 120 is connected to an end of a wire (e.g., a delivery wire) 130. Another portion (e.g., a second portion) of the sheath 120 is split longitudinally into two halves 120a, 120b. The ends 125a, 125b of each of the two halves 120a, 120b of the second portion of the sheath 120 are attached to an end of a shaft (e.g., a laser-cut, stainless-steel hypotube) 140. The diameter of the sheath 120 is uniform, or relatively uniform throughout. The diameter of the sheath 120 may be equal, or approximately equal, to a diameter of the shaft 140. The diameter of the sheath 120 may be approximately 0.01 inches, 0.02 inches, 0.03 inches, 0.04 inches, 0.05 inches, 0.06 inches, 0.07 inches, 0.08 inches, 0.09 inches, or 0.1 inches, where any value can form an upper or a lower end point of a range for diameter 150, as appropriate. The manufacturing of the sheath 120 is illustrated in FIGS. 6, 7, and 8, and discussed in the corresponding description of those figures.

In the delivery system 100 of FIG. 1, a delivery tip 150 is coupled to the wire 130, where one or more holes and/or grooves may be formed on the delivery tip 150. A stent 110 is encased within the sheath 120, and is connected to the wire 130 via the delivery tip 150. The stent 110 comprises a metallic (e.g., nitinol or stainless steel) mesh (e.g., micromesh).

The delivery system 100 may also include a catheter (e.g., a microcatheter) 170. The catheter 170 is composed of, or includes, a low-friction material, such as polytetrafluoroethylene (PTFE) (e.g., TEFLON®), or other low friction material. It should be noted that in some embodiments, the delivery system 100 does not include the catheter 170. The sheath 120, the shaft 140, the wire 130, and/or the delivery tip 150 may be positioned inside catheter 170 (e.g., pushed from a distal end of the catheter 170 to a proximal end of the catheter 170). As such, an endovascular device (e.g., a stent 110 (such as a covered stent or a therapeutic delivery stent), or other endovascular device) may be assembled in the delivery system 100.

The sheath 120 is composed of, or includes, a low-friction material such as PTFE, or other low-friction material.

The sheath 120 has a thin wall with a thickness of, for example, less than approximately 0.005 inches, less than approximately 0.004 inches, less than approximately 0.003 inches, less than approximately 0.002 inches, or less than approximately 0.001 inches. The thickness of the thin wall may be, for example, approximately 0.0001 inches, 0.0005 inches, 0.001 inches, 0.002 inches, 0.003 inches, 0.004 inches, or 0.005 inches, where any value can form an upper or a lower end point of a range for the thickness of the thin wall for the sheath 120, as appropriate. The term "approximately," as used herein when referring to a measurable value is meant to encompass variations of ±20 percent (%), ±10%, ±5%, ±1%, ±0.5%, or ±0.1% of the specified value. The sheath 120 has an outer surface configured to contact the inner surface of catheter 170, and an inner surface configured to contact the endovascular device (e.g., the stent 110).

The shaft 140 is tubular in shape, and has a proximal end, a distal end coupled with the sheath 120 (e.g., coupled with the ends 125a, 125b of the sheath 120), and an inner lumen extending therethrough. The wire 130 is disposed within the inner lumen of the shaft 140, and extends along the longitudinal length of the shaft 120. The wire 130 is configured to be selectively moved along the shaft 140 in a longitudinal direction.

The wire 130 is connected to the delivery tip 150, which in turn is configured to be selectively coupled with a proximal end of the endovascular device (e.g., the stent 110). When the endovascular device (e.g., the stent 110) is placed in the delivery system 100, the endovascular device is disposed within the inner lumen of the sheath 120, with the circumferential outer surface of endovascular device contacting the inner surface of the sheath 120, and the proximate end of the endovascular device is coupled with the delivery tip 150.

The catheter 170 is tubular in shape, and has a proximal end, a distal end, and an inner lumen extending therethrough. The catheter 170 is composed of, or includes, a low-friction material such as PTFE, or other low-friction material. The catheter 170 is configured to contain the sheath 120, the endovascular device (e.g., the stent 110) disposed within the sheath 120, the shaft 140, and the wire 130 disposed within the shaft 140. The shaft 140 is configured to be selectively moved relative to catheter 170 in the longitudinal direction. The sheath 120 is configured to be selectively and slidingly moved relative to the catheter 170 in the longitudinal direction.

During operation, in one or more embodiments, the endovascular device (e.g., stent 110) is coupled with wire 130 by coupling the endovascular device with the delivery tip 150 (e.g., using holes or grooves) at the distal end of the wire 130. For example, solder bumps formed on endovascular device (e.g., the stent 110) may be engaged with holes and/or grooves on the delivery tip 150. The endovascular device is covered (e.g., encased) by the sheath 120.

In addition, the endovascular device (e.g., stent 110), surrounded with sheath 120, is inserted into the catheter 170. For example, the endovascular device, covered by the sheath 120, may be packaged in an introducer sheath (also referred to as a packaging sheath) and, then, transferred to the catheter 170. The introducer sheath may be a PTFE tubing with a length of between, for example, four (4) inches and thirty (30) inches with a diameter (e.g., an inner diameter, a mean diameter, or an outer diameter) that is equal to, or approximately equal to, a diameter (e.g., an inner diameter, a mean diameter, or an outer diameter) of the catheter 170. The endovascular device, covered by the sheath 120, may be crimped and pulled into the introducer sheath by pulling the shaft 140 and/or the wire 130 relative to the introducer sheath.

When the endovascular device (e.g., the stent 110) is ready to be implanted at a target blood vessel, the endovascular device, covered by the sheath 120, may be transferred to a proximal end of the catheter 170 (e.g., by pushing the shaft 140 and/or the wire 130 relative to the inducer sheath and the proximal end of catheter 170 to slidingly push the endovascular device, covered by the sheath 120, from the inducer sheath to the proximal end of the catheter 170). Then, the endovascular device, covered by the sheath 120, may be pushed to the distal end of the catheter 170 as shown in FIG. 1A (e.g., by pushing the shaft 140 and/or the wire 130 relative to the catheter 170 in the longitudinal direction to slidingly push endovascular device, covered by the sheath 120, through the catheter 170).

Figure 2:
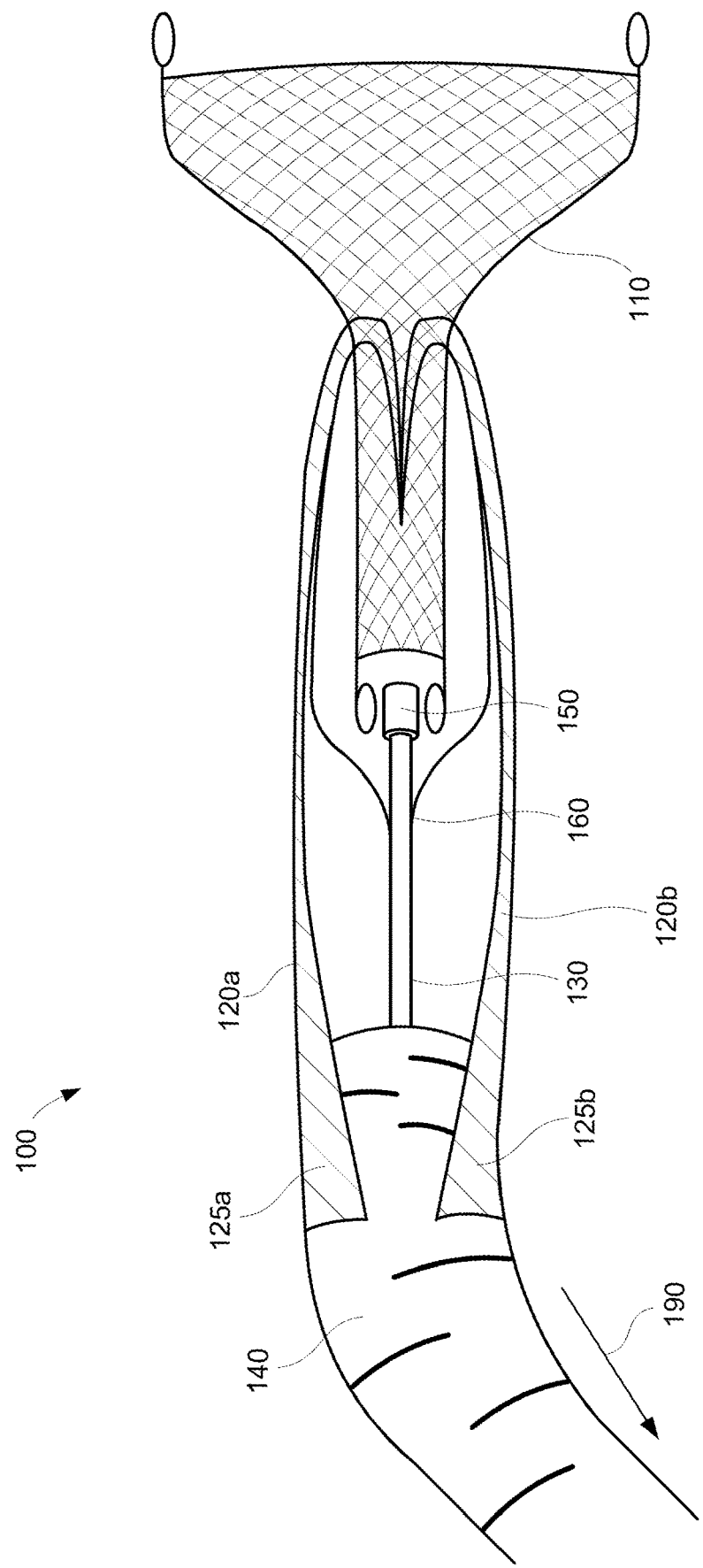
Figure 3:
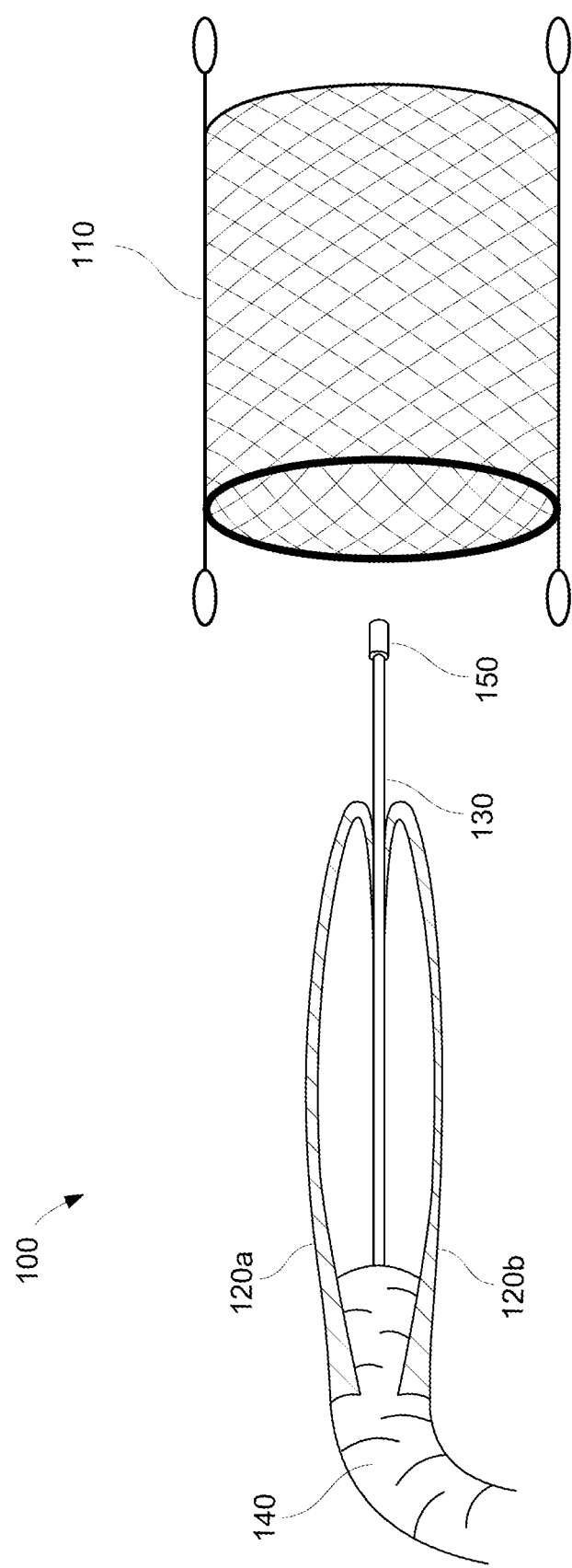

To deploy the endovascular device (e.g., the stent 110), the shaft 140 and/or the wire 130 is pushed relative to the catheter 170 in direction 122 (also referred to as the direction of delivery force), as shown in FIG. 1A, to slidingly push the sheath 120 and the endovascular device (e.g., the stent 110) along the catheter 170 to the distal end of the catheter 170, as shown in FIG. 1A. Then, the sheath 120 and the endovascular device (e.g., the stent 110) will be pushed out of the catheter 170 at a target blood vessel of a patient as shown in FIGS. 2 and 3. The sheath 120 is expandable, such that since the endovascular device (e.g., the stent 110) is a self-expanding device, the sheath 120 radially expands with the endovascular device, when the sheath 120 is pushed out of the catheter 170.

Because both the sheath 120 and the catheter 170 are composed of, or include, a low-friction material, the sheath 120 may slidingly move relative to the catheter 170, with less friction as compared to the friction between the inner surface of conventional catheters and endovascular devices. For example, both the sheath 120 and the catheter 170 may comprise PTFE, thereby resulting in PTFE-to-PTFE contact, which has very low friction. Accordingly, the low friction between the sheath 120 and the catheter 170 facilitates the pushing of the endovascular device (e.g., the stent 110) through the catheter 170 with less resistance compared to conventional catheters.

Advantageously, the delivery system 100 (through use of a sheath 120) protects the outer surface of the endovascular device (e.g., the stent 110) from contact with the inner surface of the catheter 170, thereby substantially decreasing the friction of the endovascular device as it traverses through the catheter 170, and is delivered to its intended target. The delivery system 100 also protects the endovascular device from shear forces as it traverses through the catheter 170, which is particularly advantageous for endovascular devices, which typically have delicate features, such as thin-film covered stents or stents intended to deliver therapeutics (e.g., proteins, small molecules, cell-based therapies, biological substrates, or other therapeutics). Shear forces generated during the delivery of these devices may damage or delaminate the thin-film, or the therapeutic, from the surface of these devices. In conventional endovascular device delivery systems, the inner surface of a catheter typically has direct contact with the endovascular devices, thereby resulting in more friction and sheer forces to be generated between the endovascular device and the inner lumen of the catheter.

Figure 1B:
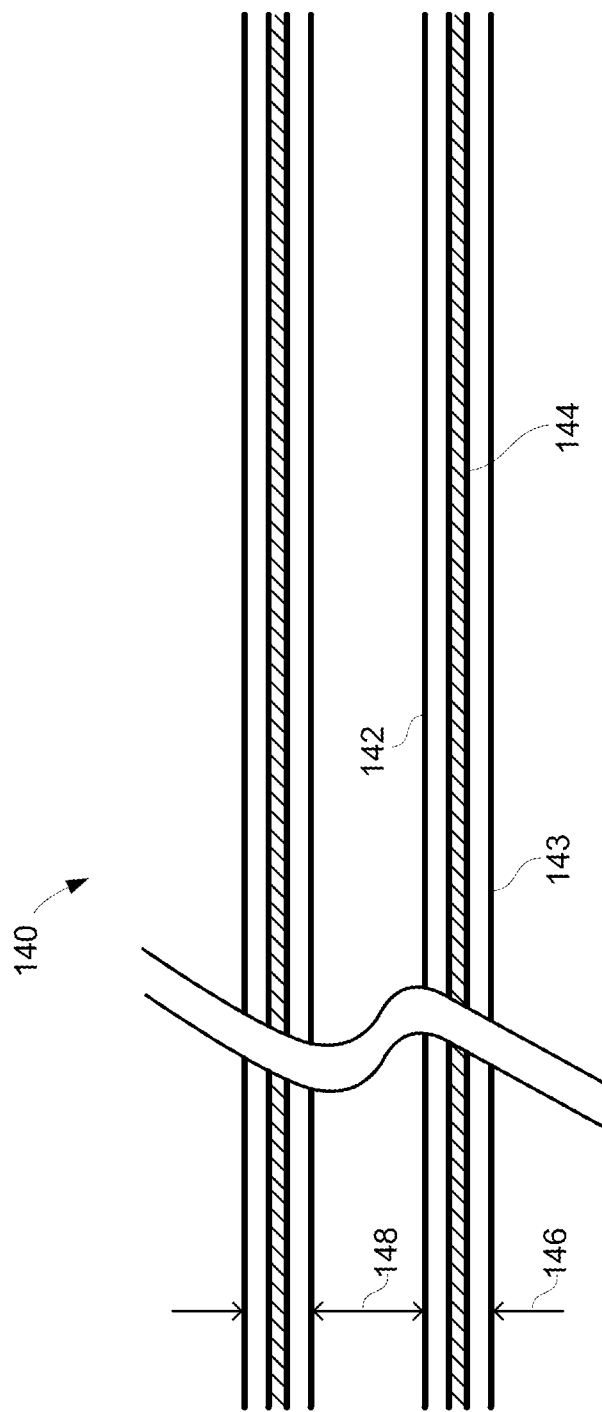

FIG. 1B is a diagram showing details of the shaft 140 of the delivery system 100 of FIG. 1A, in accordance with at least one embodiment of the present disclosure. The shaft 140 includes an outer jacket 143, an inner liner 142, and braided tubing 144. The outer jacket 143 of the shaft 140 is tubular in shape, and has a proximal end, a distal end, and an inner lumen extending therethrough. The outer jacket 143 may be composed of, or includes, a thermoplastic elastomer (TPE) material such as a polyether block amide (PEBA) material (e.g., PEBAX® or other polyether block amide material). The outer jacket 143 may have a diameter 146 (e.g., an outer diameter, a mean diameter, or an inner diameter) between approximately 0.01 inches and approximately 0.1 inches. The diameter 146 may be the outer diameter of the shaft 140. The diameter 146 may be approximately 0.01 inches, 0.02 inches, 0.03 inches, 0.04 inches, 0.05 inches, 0.06 inches, 0.07 inches, 0.08 inches, 0.09 inches, or 0.1 inches, where any value can form an upper or a lower end point of a range for diameter 146, as appropriate.

The inner liner 142 of the shaft 140 is tubular in shape, and has a proximal end, a distal end, and an inner lumen extending therethrough. The inner liner 142 is disposed within the outer jacket 143, and extends along the longitudinal direction of the outer jacket 143. The inner liner 142 may be composed of, or includes, a low-friction material such as PTFE, or other low-friction material. The inner liner 142 has a thin wall with a thickness of, for example, less than approximately 0.005 inches, less than approximately 0.004 inches, less than approximately 0.003 inches, less than approximately 0.002 inches, or less than approximately 0.001 inches. The thickness of the thin wall may be, for example, approximately 0.0001 inches, 0.0005 inches, 0.001 inches, 0.002 inches, 0.003 inches, 0.004 inches, or 0.005 inches, where any value can form an upper or a lower end point of a range for the thickness of the thin wall, as appropriate. The inner liner 142 may have a diameter 148 (e.g., an outer diameter, a mean diameter, or an inner diameter of the inner liner 142) between approximately 0.005 inches and approximately 0.1 inches. The diameter 148 may be the inner diameter of the shaft 140. The diameter 148 may be approximately 0.005 inches, 0.01 inches, 0.02 inches, 0.03 inches, 0.04 inches, 0.05 inches, 0.06 inches, 0.07 inches, 0.08 inches, 0.09 inches, or 0.1 inches, where any value can form an upper or a lower end point of a range for the inner diameter, as appropriate.

The braided tubing 144 is tubular in shape, and has a proximal end, a distal end, and an inner lumen extending therethrough. The braided tubing 144 is disposed between the outer jacket 143 and the inner liner 142, and extends along the longitudinal direction of the outer jacket 143 and the inner liner 142. The braided tubing 144 may be a tube formed from a braided mesh of wires. The braided tubing 144 has a diameter (e.g., an inner diameter, a mean diameter, or an outer diameter) that is intermediate of the diameter 146 of the outer jacket 143 and the diameter 148 of the inner lining 142.

FIG. 1C is a diagram showing details of an exemplary wire 130 of the delivery system 100 of FIG. 1A, in accordance with at least one embodiment of the present disclosure. The wire 130 includes a proximal section 158 and a coiled distal section 163. The proximal section 158 and/or the coiled distal section 163 may be composed of, or include, stainless steel, nitinol, and/or tungsten. Most of the length (e.g., more than half, more than 90%, more than 99%, etc.)

of the wire 130 may be the proximal section 158, and the rest (e.g., less than half, less than 10%, less than 1%, etc.) of the wire 130 may be the coiled distal section 163. The coiled distal section 163 is coiled for flexibility, and may be more flexible than the proximal section 158 of the wire 130.

FIG. 1D is a diagram showing details of an exemplary one-piece delivery tip 150a of the delivery system 100 of FIG. 1A, in accordance with at least one embodiment of the present disclosure. In one or more embodiments, the one-piece delivery tip 150a may be employed for the delivery tip 150 of the delivery system 100 of FIG. 1A. The delivery tip 150a of FIG. 1D is tubular, and includes a proximal section 162a, an intermediate section 164a, and a distal section 166a. An outer diameter of the proximal section 162a may be larger than an outer diameter of the intermediate section 164a, such that a step 168 is formed between the proximal section 162a and the intermediate section 164a. Holes and/or grooves 116a are formed on the intermediate section 164a to engage a proximal end of the endovascular device (e.g., the stent 110). In one or more embodiments, the distal section 166a may include slits 171a for flexibility. The delivery tip 150a may be composed of, or include, stainless steel, nitinol, and/or tungsten. In one example, the proximal section 162a may have an outer diameter of approximately 0.025 inches, and an inner diameter of between 0.016 inches and 0.018 inches. The intermediate section 164a may have an outer diameter of approximately 0.020 inches, and an inner diameter of between approximately 0.016 inches and approximately 0.018 inches. The outer diameter of the delivery tip 150a varies from approximately 0.025 inches to approximately 0.020 inches at step 164.

FIG. 1E is a diagram showing details of the one-piece delivery tip 150a of FIG. 1D assembled on the wire 130 of FIG. 1C of the delivery system 100 of FIG. 1A, in accordance with at least one embodiment of the present disclosure. The delivery tip 150a may be attached to the coiled distal section 163 of the wire 130 with an adhesive 172, such as ultraviolet (UV) polymer adhesive (glue) or solder.

FIGS. 1F and 1G are diagrams showing details of an exemplary two-piece delivery tip 150b of the delivery system 100 of FIG. 1A, in accordance with at least one embodiment of the present disclosure. In one or more embodiments, the two-piece delivery tip 150b may be employed for the delivery tip 150 of the delivery system 100 of FIG. 1A. The delivery tip 150b may include two parts 174 and 176, as shown in FIGS. 1F and 1G, respectively. FIG. 1F is a diagrammatic side-view of part 174 of the delivery tip 150b, and FIG. 1G is a diagrammatic side-view of part 176 of the delivery tip 150b. Parts 174 and 176 may be composed of, or include, stainless steel, nitinol, and/or tungsten. The delivery tip 150b of FIGS. 1F and 1G together is tubular, and includes a proximal section 162b, an intermediate section 164b, and a distal section 166b. Holes and/or grooves 116b are formed on the intermediate section 164b to engage a proximal end of the endovascular device (e.g., the stent 110). In one or more embodiments, the distal section 166b may include slits 171b for flexibility. In one example, part 174 has an outer diameter of approximately 0.025 inches, and an inner diameter of between approximately 0.016 inches and approximately 0.018 inches. Part 176 has an outer diameter of approximately 0.020 inches, and an inner diameter of between approximately 0.016 inches and approximately 0.018 inches.

FIG. 1H is a diagram showing details of the two-piece delivery tip 150b of FIGS. 1F and 1G assembled on the wire 130 of FIG. 1C of the delivery system 100 of FIG. 1A, in accordance with at least one embodiment of the present disclosure. Part 174 of the delivery tip 150b may be attached to the coiled distal section 163 of the wire 130 with an adhesive 178, such as a UV polymer adhesive (glue) or solder. And, part 176 may also be attached to the coiled distal section 163 of the wire 130 with an adhesive 180, such as a UV polymer adhesive (glue) or solder.

It should be noted that in some embodiments, the wire 130 itself includes the delivery tip 150 (e.g., 150a, 150b). The delivery tip 150 may be formed at the distal end of the wire 130, such that the delivery tip 150 is not a separate piece(s), but rather is integrated within the wire 130.

Figure 1I:
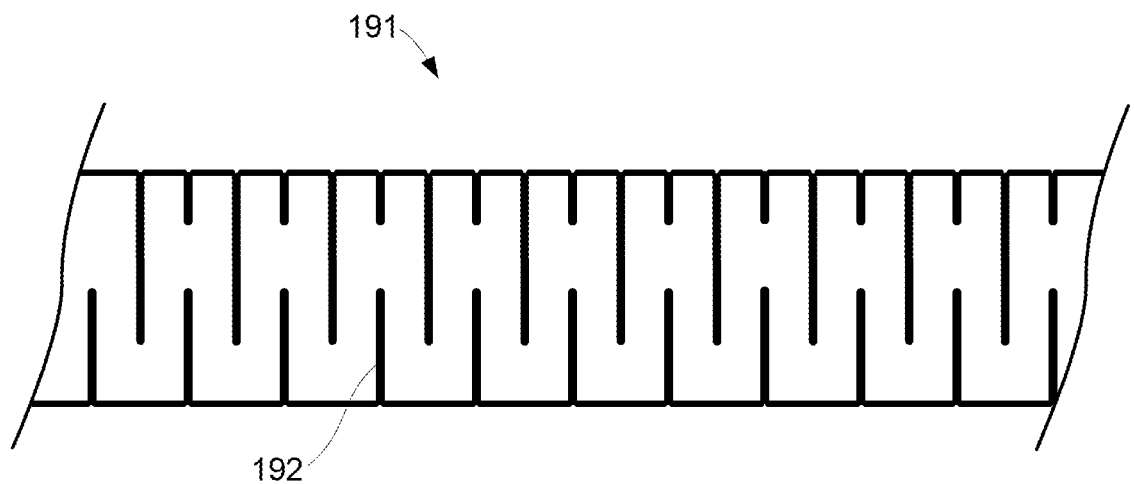

FIG. 1I is an image of an exemplary laser-cut shaft 191 that may be employed for the shaft 140 of FIG. 1A, in accordance with at least one embodiment of the present disclosure. The shaft 191 of FIG. 1I is a laser-cut metallic (e.g., stainless-steel) hypotube. The shaft 191 comprises a plurality of laser cuts 192. The flexibility of the shaft 191 is related (e.g., directly proportional) to the density of the laser cuts 192 on the shaft 191. As such, the higher the density of the laser cuts 192, the more flexible the shaft 191 will be.

Figure 1J:
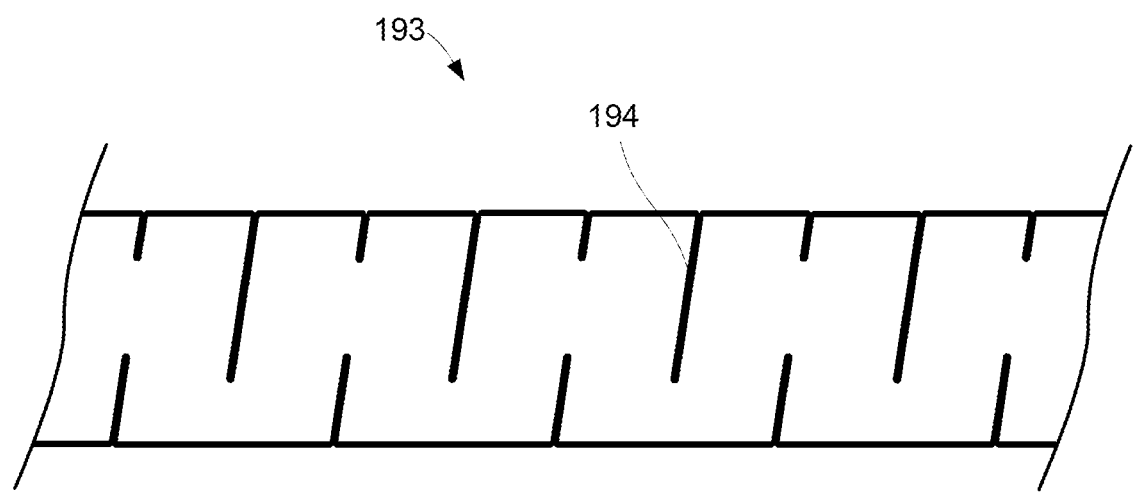

FIG. 1J is an image of another exemplary laser-cut shaft 193 that may be employed for the shaft 140 of FIG. 1A, in accordance with at least one embodiment of the present disclosure. Similar to the shaft 191 of FIG. 1I, the shaft 193 of FIG. 1J is a laser-cut metallic (e.g., stainless-steel) hypotube and comprises a plurality of laser cuts 194. The density of the laser cuts 194 on the shaft 193 of FIG. 1J is less than the density of the laser cuts 192 on the shaft 191 of FIG. 1I. Since the shaft 191 has a higher density of laser cuts 192 than the density of the laser cuts 194 on the shaft 193, the shaft 191 is more flexible than the shaft 193.

Figure 1K:
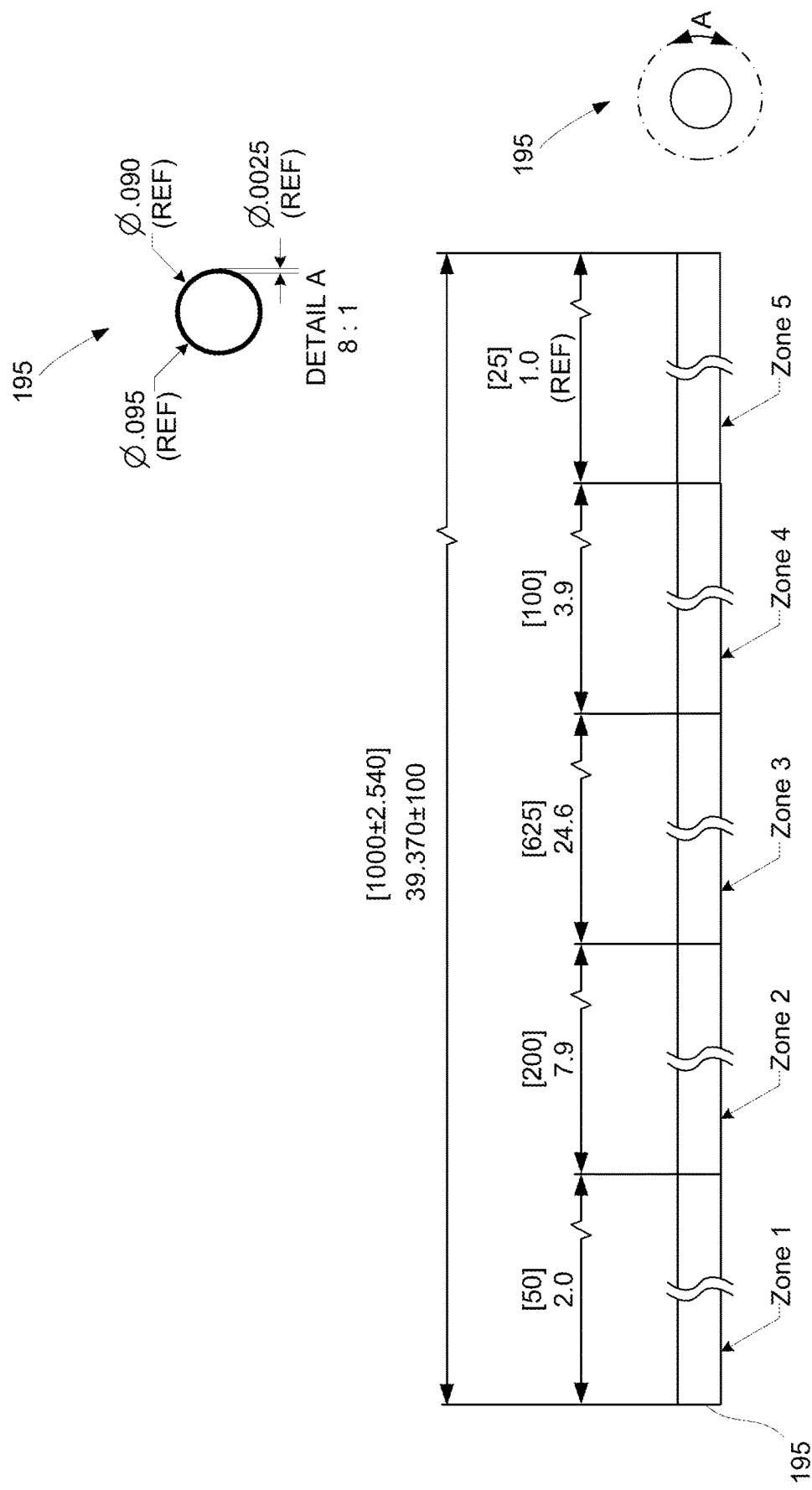

FIG. 1K is a schematic diagram showing details of an exemplary laser-cut shaft 195 that may be employed for the shaft 140 of FIG. 1A, in accordance with at least one embodiment of the present disclosure. The shaft 195 of FIG. 1K is a laser-cut metallic (e.g., stainless-steel) hypotube. The shaft 195 has an approximate total length of 1000+/−2.540 centimeters (cm) (or 39.370+/−0.100 inches (in)). Also, the shaft 195 is shown to comprise a plurality of zones (i.e. zone 1, zone 2, zone 3, zone 4, and zone 5). Each zone of the shaft 195 has its own specific length. For example, zone 1 is 50 cm (or 2.0 in) in length, zone 2 is 200 cm (or 7.9 in) in length, zone 3 is 625 cm (or 24.6 in) in length, zone 4 is 100 cm (or 3.9 in) in length, and zone 5 is 25 cm (or 1.0 in) in length. Also, the shaft 195 has an inner diameter of 0.090 inches and an outer diameter of 0.095 inches. However, it should be noted that, in other embodiments, the shaft 195 may be manufactured to comprise various different numbers of zones with various different lengths and/or various different sizes of inner and/or outer diameters than as shown in FIG. 1K.

Each of the zones (i.e. zone 1, zone 2, zone 3, zone 4, and zone 5) of the shaft 195 may comprise a pattern of laser cuts or may comprise no laser cuts at all. The density of the laser cuts varies along the length of the shaft 195, and the flexibility of the shaft 195 is dependent upon the density of the laser cuts. In one or more embodiments, the laser cut patterns are chosen for the zones to give the shaft 195 an increasing flexibility from the proximal end of the shaft 195 to the distal end of the shaft 195.

For example, in one or more embodiments, zone 1 of the shaft 195 has no laser cuts at all; zone 2 of the shaft 195 has 3.5 cuts per revolution (CPR) around the shaft 195 with a pitch of 0.0027 to 0.014 with a cut pattern of 96 degrees (°) cut/6.85° uncut to 81° cut/21.85° uncut, zone 3 of the shaft 195 has 3.5 CPR around the shaft 195 with a pitch of 0.014 with a cut pattern of 81° cut/21.85° uncut, zone 4 of the shaft 195 has 3.5 CPR around the shaft 195 with a pitch of 0.014 with a cut pattern of 81° cut/21.85° uncut to 61° cut/41.85° uncut, and zone 5 of the shaft 195 has 3.5 CPR around the shaft 195 with a pitch of 0.0027 with a cut pattern of 96 degrees (°) cut/6.85°. It should be noted that, in other embodiments, the zones on the shaft 195 may comprise various different cut patterns than these exemplary cut patterns given for FIG. 1K.

FIG. 2 is a diagram showing the disclosed delivery system 100 of FIG. 1, where the sheath 120 is split open and the stent 110 is partially unsheathed, in accordance with at least one embodiment of the present disclosure. After the endovascular device (e.g., stent 110), covered by the sheath 120, is pushed to the distal end of the catheter 170 (not shown in FIG. 2) as is shown in FIG. 1A, for deployment of the stent 110 to the target area in the patient, the shaft 140 is pulled back (e.g., by a user, such as a physician or clinician) relative to the wire 130. The pulling back of the shaft 140 (in the direction 190) relative to the wire 130 causes the portion (e.g., the first portion) of the sheath 120 (which is circumferentially intact) to split open longitudinally along the length of the sheath 120, which unsheathes and exposes the stent 110. As the stent 110 becomes exposed from the sheath 120, the stent 110, being self-expanding, expands out to deploy.

It should be noted that since the sheath 120 is folded back onto itself (e.g., refer to FIGS. 6, 7, and 8), the distance of pulling back of the shaft 140 in relation to a distance of unsheathing of the stent 110 is approximately a two to one ratio, such that every two units of distance of pulling back of the shaft 140 causes approximately one unit of distance of unsheathing of the stent 110.

FIG. 3 is a diagram showing the disclosed delivery system 100 of FIG. 1, where the stent 110 is fully deployed, in accordance with at least one embodiment of the present disclosure. As shown in FIG. 3, after the stent 110 has become fully unsheathed and exposed from the sheath 120, the stent 110 is released (and disengaged) from the wire 130 via the delivery tip 150. After the stent 110 is released from the wire 130, the stent 110 is thus deployed to the target area (e.g., blood vessel) of the patient. After the stent 110 is deployed to the target area, the sheath 120 and the wire 130 are pulled back into the catheter 170 (not shown in FIG. 3), and the catheter 170 (containing the remaining components of the delivery system 100, other than the stent 110) is removed from the patient.

Figure 4:
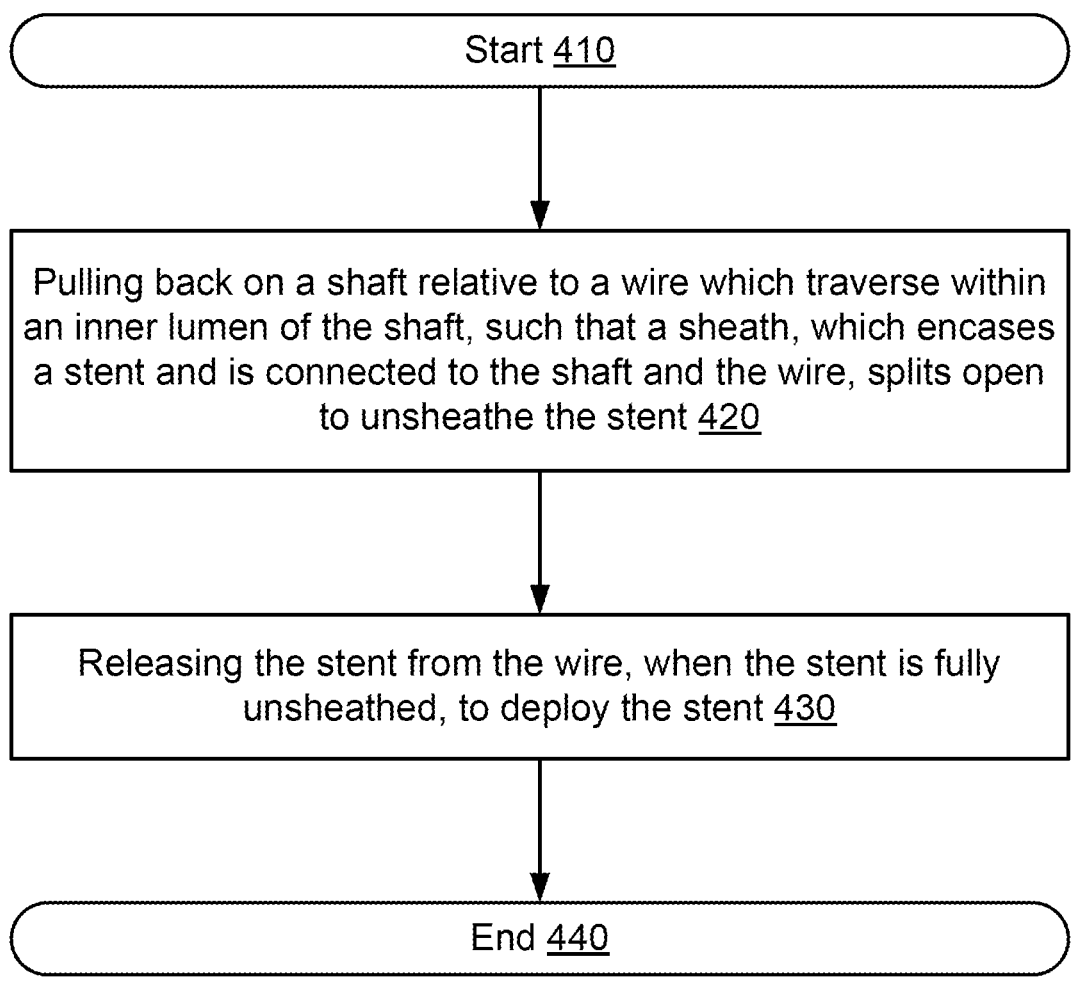
FIG. 4 is flow chart showing the disclosed method for operation of the disclosed delivery system for endovascular devices, in accordance with at least one embodiment of the present disclosure.

FIG. 4 is flow chart showing the disclosed method 400 for operation of the disclosed delivery system for endovascular devices, in accordance with at least one embodiment of the present disclosure. At the start 410 of the method 400, the shaft is pulled back relative to the wire, which traverses within an inner lumen of the shaft, such that a sheath, which encases the stent and is connected to the shaft and the wire, splits open to unsheathe the stent 420. Then, when the stent is fully unsheathed, the stent is released from the wire to deploy the stent 430. Then, the method 400 ends 440.

Figure 5:
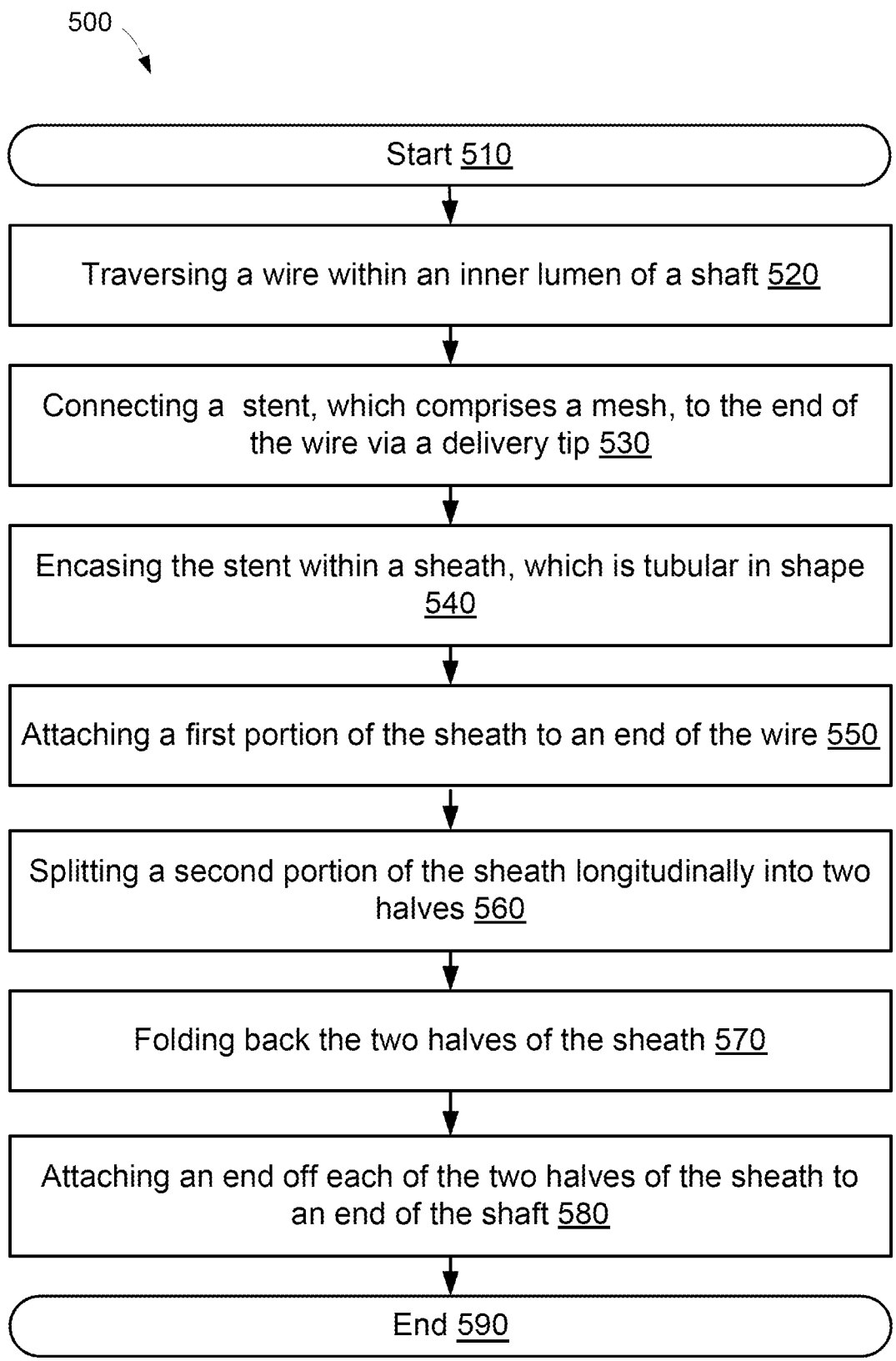
FIG. 5 is a flow chart showing the disclosed method of manufacture for the disclosed delivery system for endovascular devices, in accordance with at least one embodiment of the present disclosure.

FIG. 5 is a flow chart showing the disclosed method 500 of manufacture for the disclosed delivery system for endovascular devices, in accordance with at least one embodiment of the present disclosure. At the start 510 of the method 500, a wire is traversed within an inner lumen of a shaft 520. Then, a stent, which comprises a mesh, is connected to an end of the wire via a delivery tip 530. The stent is encased within a sheath, which is tubular in shape 540. Then, a first portion of the sheath is attached to an end of the wire 550. And, a second portion of the sheath is split longitudinally into two halves 560. The two halves of the second portion of the sheath are folded back 570. Then, an each of the ends of the two halves of the sheath are attached to an end of the shaft 580. Then, the method 500 ends 590.

FIGS. 6, 7, and 8 are diagrams that together illustrate a portion of the method of manufacture of the delivery system 600 for endovascular devices, in accordance with at least one embodiment of the present disclosure. In particular, FIG. 6 is a diagram showing the stent 610 encased within the sheath 620 for the disclosed delivery system 600 for endovascular devices, in accordance with at least one embodiment of the present disclosure. In this figure, the delivery system 600 is shown to comprise a stent 610 encased within a sheath 620, where the stent 610 is attached to a wire 630 via a delivery tip 650. Also shown is a shaft 640 attached to the wire 630. An end 660 of the sheath 620 is connected to the shaft 640. In one or more embodiments, the end 660 of the sheath 620 is connected to the shaft 640 via adhesive (e.g., glue or other adhesive), soldering, a wire, a string, tubing, and/or other means of fastening.

FIG. 7 is a diagram showing a portion of the sheath 620 split longitudinally into two halves 620a, 620b for the disclosed delivery system 600 for endovascular devices, in accordance with at least one embodiment of the present disclosure. In this figure, a portion (e.g., a first portion) of the sheath 620 is split longitudinally into two separate halves 620a, 620b. The two halves 620a, 620b are then folded back (in directions 690a, 690b, respectively) towards another portion (e.g., a second portion) of the sheath 620, which remains circumferentially intact.

FIG. 8 is a diagram showing the two halves 620a, 620b of the sheath 620 folded back and attached to an end of the shaft 640 for the disclosed delivery system 600 for endovascular devices, in accordance with at least one embodiment of the present disclosure. In this figure, the two halves 620a, 620b of the sheath 620 have been folded back and are laying on the exterior surface of the portion (e.g., second portion) of the sheath 620 that remains circumferentially intact. The ends 625a, 625b of each of the two halves 620a, 620b of the sheath 620 are attached to an end of the shaft 640. In one or more embodiments, the ends 625a, 625b of the sheath 620 are attached to the end of the shaft 640 via adhesive (e.g., glue or other adhesive), soldering, a wire, a string, tubing, and/or other means of fastening.

Figure 9:
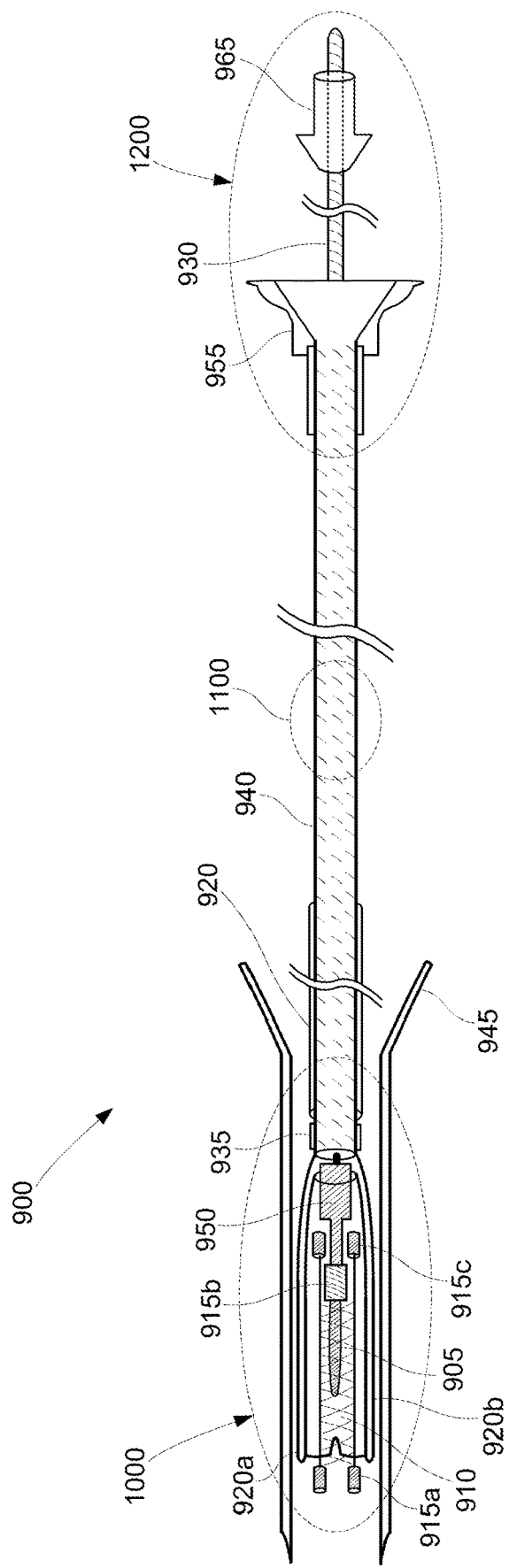
FIG. 9 is a detailed diagram of the disclosed delivery system for endovascular devices, in accordance with at least one embodiment of the present disclosure.

FIG. 9 is a detailed diagram of the disclosed delivery system 900 for endovascular devices, in accordance with at least one embodiment of the present disclosure. In particular, FIG. 9 shows an exemplary embodiment for the disclosed delivery system 900. In this figure, the delivery system 900 is shown to comprise three portions, which are a first portion 1000, a second portion 1100, and a third portion 1200.

The first portion 1000 comprises a stent 910 encased within a sheath 920, which comprises two halves 920a and 920b folded back onto the sheath 920. The ends of the two halves 920a, 920b of the sheath 920 are attached to a stainless-steel shaft 940 via a polyimide sleeve 935. The stent 910 is attached to an end of a wire (e.g., a stainless-steel wire or a nitinol wire) 930 via a stainless-steel delivery tip (e.g., a pusher tip) 950. A distal floppy wire 905, which is connected to the end of the wire 930, lies within the stent 910. Radio/opaque (R/O) marker bands 915a, 915b, 915c are located on the distal end and within the sheath 920. The sheath 920 is encased within an introducer sheath 945, which comprises transparent PTFE.

Figure 10:
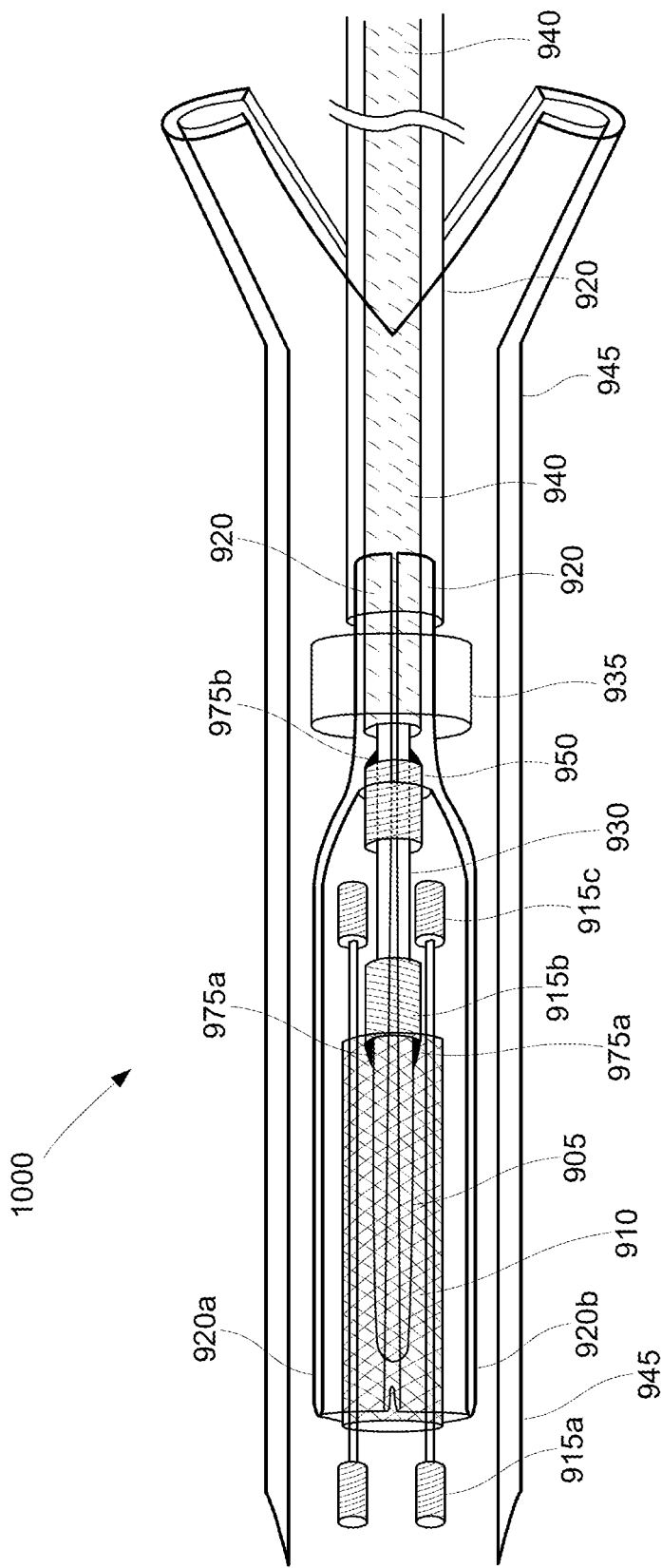
FIG. 10 is a detailed diagram of a first portion of the disclosed delivery system of FIG. 9, in accordance with at least one embodiment of the present disclosure.

FIG. 10 is a detailed diagram of a first portion 1000 of the disclosed delivery system 900 of FIG. 9, in accordance with at least one embodiment of the present disclosure. In this detailed diagram, the R/O marker band 915b is soldered 975a onto the distal floppy wire 905. Also, the stainless-steel delivery tip 950 is soldered 975b onto the end of the wire 930. The stainless-steel shaft 940 is laser-cut 940.

Figure 11:
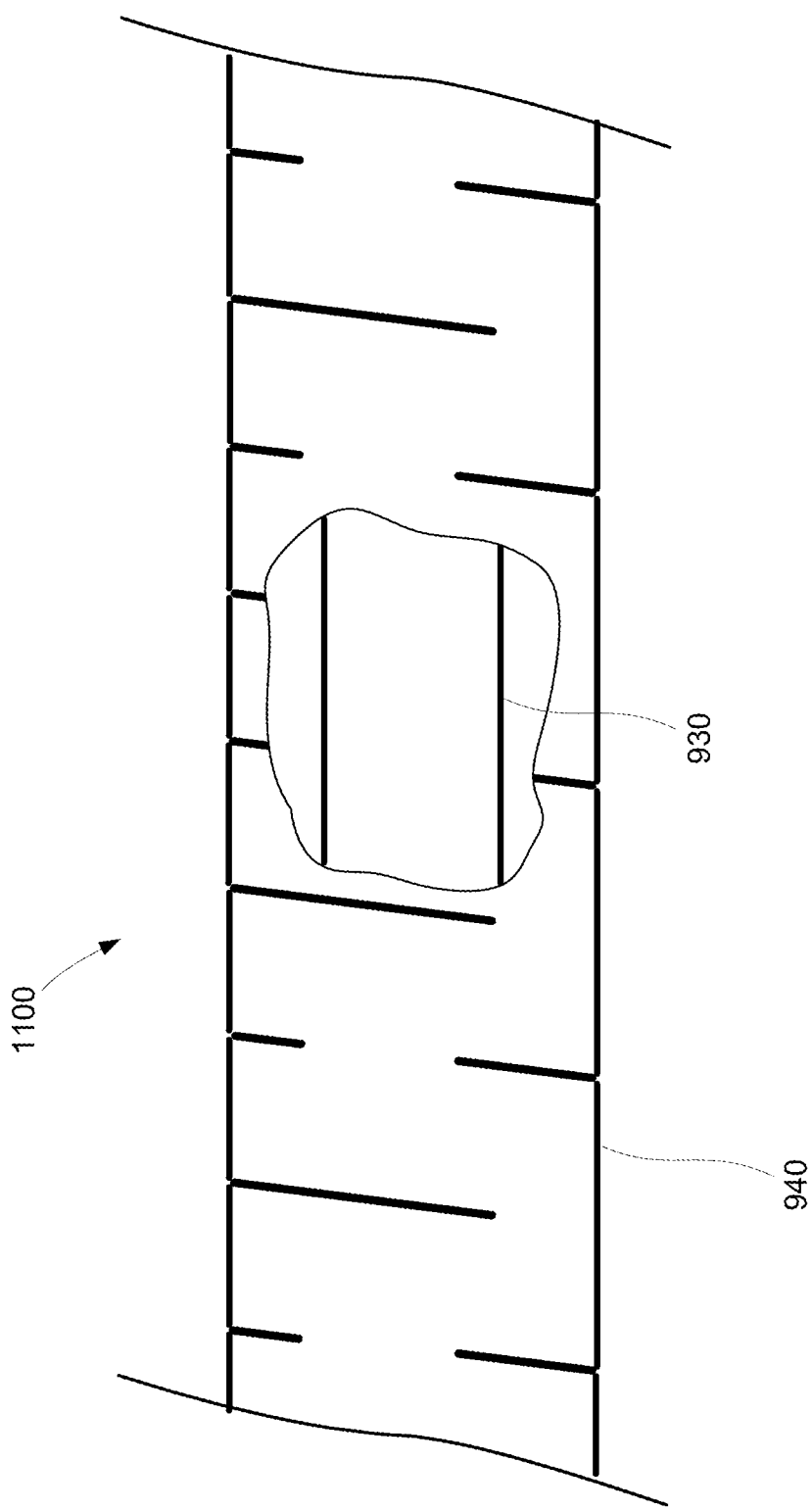
FIG. 11 is a detailed diagram of a second portion of the disclosed delivery system of FIG. 9, in accordance with at least one embodiment of the present disclosure.

FIG. 11 is a detailed diagram of a second portion 1100 of the disclosed delivery system 900 of FIG. 9, in accordance with at least one embodiment of the present disclosure. The second portion 1100 comprises the wire 930 traversing within an inner lumen of the laser-cut stainless-steel shaft 940.

Figure 12:
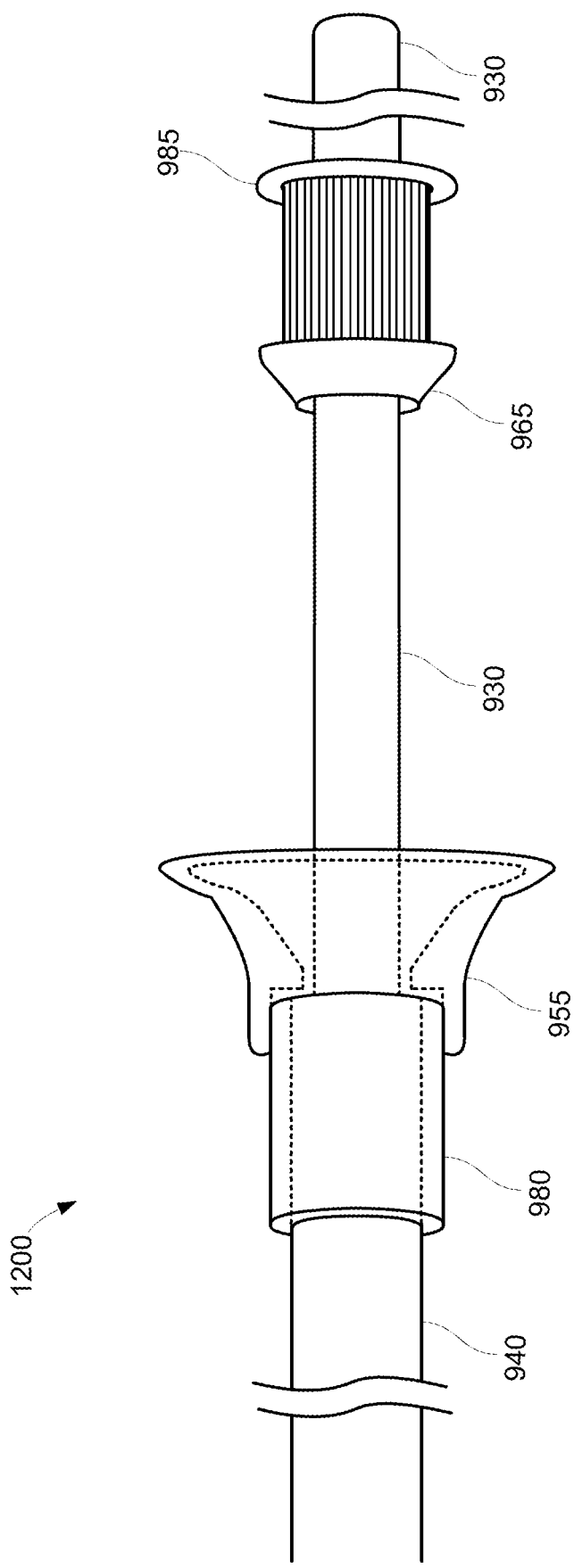
FIG. 12 is a detailed diagram of a third portion of the disclosed delivery system of FIG. 9, in accordance with at least one embodiment of the present disclosure.

FIG. 12 is a detailed diagram of a third portion 1200 of the disclosed delivery system 900 of FIG. 9, in accordance with at least one embodiment of the present disclosure. The third portion 1200 comprises a wire gripper (e.g., a torquer) 965 attached to an end of the wire 930. The ring 985 located at the base of the wire gripper 965 is rotated to tighten, or to loosen, the grip onto the wire 930. The wire 930 traverses into the shaft 940 through a shaft hub 955 and a strain-relief jacket 980. The shaft hub 955 is attached (e.g., via glue or adhesive) to the strain-relief jacket 980. In addition, the strain-relief jacket 980 is attached to the shaft 940 via a fluorinated ethylene propylene (FEP) heat shrink.

Figure 13:
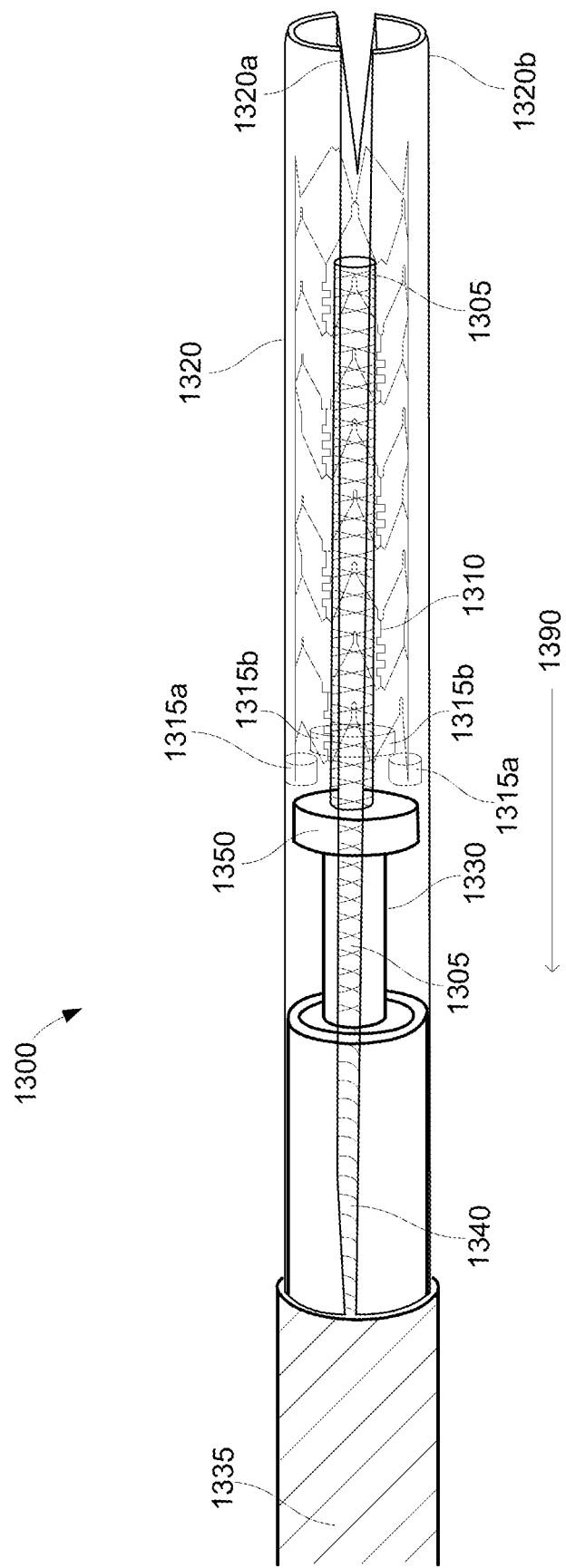
FIG. 13 is a detailed diagram of the disclosed delivery system for endovascular devices, in accordance with at least one embodiment of the present disclosure.

FIG. 13 is a detailed diagram of the disclosed delivery system 1300 for endovascular devices, in accordance with at least one embodiment of the present disclosure. The disclosed delivery system 1300 comprises a stent (e.g., a TITAN® stent) 1310 crimped down and encased within a sheath 1320, which comprises two halves 1320a, 1320b that are reverted and folded back. R/O marker bands 1315a on the proximal end of the stent 1320 interface with R/O marker bands 1315b on a corewire (e.g., distal floppy wire) of a steerable wire 1330. A proximal end of the stent 1310 is attached to the end of the steerable wire 1330 via a delivery tip 1350, which is a mechanical interface with the proximal end of the stent 1310 for pushing the stent 1310. The steerable wire 1330 traverses through the center of a shaft (e.g., a laser-cut stainless-steel hypotube) 1340. The ends of the two halves 1320a, 1320b of the sheath 1320 are secured onto the shaft 1340 via thin-wall heat-shrink tubing 1335.

Where methods described above indicate certain events occurring in certain order, those of ordinary skill in the art having the benefit of this disclosure would recognize that the ordering may be modified and that such modifications are in accordance with the variations of the present disclosure. Additionally, parts of methods may be performed concurrently in a parallel process when possible, as well as performed sequentially. In addition, more steps or less steps of the methods may be performed.

Although certain illustrative embodiments and methods have been disclosed herein, it can be apparent from the foregoing disclosure to those skilled in the art that variations and modifications of such embodiments and methods can be made without departing from the true spirit and scope of this disclosure. Many other examples exist, each differing from others in matters of detail only. Accordingly, it is intended that this disclosure be limited only to the extent required by the appended claims and the rules and principles of applicable law.

We claim:

1. A delivery system, the system comprising:
a stent comprising a mesh;
a shaft comprising an inner lumen;
a sheath encasing the stent, wherein the stent and a first portion of the sheath are connected to an end of a wire, the first portion of the sheath is circumferentially intact, a second portion of the sheath is split longitudinally into two halves, the two halves are folded back over the first portion of the sheath, and the two halves are connected to an end of the shaft; and
the wire traversing within the inner lumen of the shaft such that when the shaft is pulled back relative to the wire, the first portion of the sheath opens thereby unsheathing and deploying the stent.

2. The system of claim 1, wherein the stent is connected to the wire via a delivery tip.

3. The system of claim 2, wherein the delivery tip comprises at least one of a hole or a groove.

4. The system of claim 1, wherein the sheath comprises polytetrafluoroethylene (PTFE).

5. The system of claim 1, wherein the mesh comprises a metallic material.

6. The system of claim 5, wherein the metallic material is one of nitinol or stainless steel.

7. The system of claim 1, wherein the shaft comprises an outer jacket, an inner liner, and a braided tubing.

8. The system of claim 7, wherein the outer jacket comprises a thermoplastic elastomer (TPE) material.

9. The system of claim 7, wherein the inner liner comprises PTFE.

10. The system of claim 7, wherein the braided tubing comprises a braided mesh of wires.

11. The system of claim 1, wherein the wire comprises at least one of stainless steel, nitinol, or tungsten.

12. The system of claim 1, wherein the shaft comprises a laser-cut stainless-steel hypotube.

13. The system of claim 12, wherein the laser-cut stainless-steel hypotube comprises a plurality of laser cuts, wherein a density of the laser cuts varies along a length of the shaft.

14. The system of claim 13, wherein a flexibility of the shaft is related to the density of the laser cuts.

15. A method for operating the delivery system of claim 1, the method comprising:
pulling back on the shaft relative to the wire, which traverses within the inner lumen of the shaft, such that the first portion of the sheath splits open to unsheathe and deploy the stent.

16. The method of claim 15, wherein a distance of pulling back of the shaft in relation to a distance of unsheathing of the stent is approximately a two to one ratio, such that every two units of distance of pulling back of the shaft causes approximately one unit of distance of unsheathing of the stent.

17. The method of claim 15, wherein the method further comprises releasing the stent from the wire, when the stent is fully unsheathed, to deploy the stent.

18. A method for manufacture of the delivery system of claim 1, the method comprising:
traversing the wire within the inner lumen of the shaft;
connecting the stent, which comprises the mesh, to the end of the wire via a delivery tip;
encasing the stent within the sheath, which is tubular in shape;
attaching the first portion of the sheath to an end of the wire;
splitting the second portion of the sheath longitudinally into the two halves;
folding back the two halves of the sheath; and
attaching the end of each of the two halves of the sheath to an end of the shaft.

* * * * *